US010196762B2

(12) United States Patent
Thomas

(10) Patent No.: US 10,196,762 B2
(45) Date of Patent: Feb. 5, 2019

(54) ENHANCED SUTURE BRAID STRENGTH THROUGH CLICK CHEMISTRY

(75) Inventor: Jonathan Thomas, New Haven, CT (US)

(73) Assignee: Covidien LP, Mansfield, MA (US)

(*) Notice: Subject to any disclaimer, the term of this patent is extended or adjusted under 35 U.S.C. 154(b) by 1313 days.

(21) Appl. No.: 13/637,162

(22) PCT Filed: Mar. 24, 2011

(86) PCT No.: PCT/US2011/029864
§ 371 (c)(1),
(2), (4) Date: Dec. 10, 2012

(87) PCT Pub. No.: WO2011/119885
PCT Pub. Date: Sep. 29, 2011

(65) Prior Publication Data
US 2013/0079816 A1    Mar. 28, 2013

Related U.S. Application Data

(60) Provisional application No. 61/317,439, filed on Mar. 25, 2010.

(51) Int. Cl.
*D02G 3/22* (2006.01)
*A61L 17/14* (2006.01)
(Continued)

(52) U.S. Cl.
CPC .............. *D02G 3/22* (2013.01); *A61L 17/145* (2013.01); *A61L 27/14* (2013.01); *A61L 31/08* (2013.01); *D02G 1/00* (2013.01); *A61L 2400/18* (2013.01)

(58) Field of Classification Search
CPC ...................... C08J 5/00; C08J 2300/10; B01J 2219/00628; B01J 20/285; B01J 20/3285;
(Continued)

(56) References Cited

U.S. PATENT DOCUMENTS 3,187,752 A    6/1965 Glick
3,565,077 A    2/1971 Glick
(Continued)

FOREIGN PATENT DOCUMENTS

EP    0542151 A1    5/1993
WO    2010095049 A1    8/2010
(Continued)

OTHER PUBLICATIONS

Fiore et al. Single and dual glycoside clustering around calix[4]arene scaffolds via click thiol-ene coupling and azide-alkyne cycloaddition, Org. Biomol. Chem., 2009,7,3910-3913.*
(Continued)

*Primary Examiner* — Scott R. Walshon

(57) ABSTRACT

The present disclosure relates to a method of forming yarns and preparing surgical devices therefrom. The yarns include at least one first filament possessing a polymer core and first reactive members known to have click reactivity on a surface thereof and at least one second filament possessing a polymer core and second reactive members known to have click reactivity on a surface thereof. The first and second reactive members are complementary such that they interact to covalently bond the filaments together.

21 Claims, 5 Drawing Sheets

(51) Int. Cl.
*A61L 27/14* (2006.01)
*A61L 31/08* (2006.01)
*D02G 1/00* (2006.01)

(58) Field of Classification Search
CPC .. B01J 20/327; B01J 20/261; B01J 20/28033; B01J 20/286; B01J 20/3078; B01J 20/3085; B01J 20/3204; B01J 20/3208; B01J 20/3246; D02G 3/22; D02G 1/00; D02G 3/00; D01D 5/34; D01D 10/00; A61L 17/145; A61L 2400/18; A61L 27/14; A61L 31/08; A61L 17/04; A61L 27/50; A61L 31/14; A61L 31/148; A61L 31/145; A61L 31/06; A61L 24/001; A61L 24/04; A61L 24/10; A61L 24/108; A61B 17/0057; A61B 2017/00641; A61B 2017/0065; A61B 2017/00676; A61F 2/0063; A61F 2/90; D01F 2/00; D01F 4/00; D01F 6/00; D01F 9/00; D01F 6/62; D01F 6/66; D01F 6/78; D01F 6/86; D06M 15/6436; D06M 14/28; D06M 14/34; D06M 15/643; D06M 14/26; B29C 47/0014; B29C 47/0004; B05D 1/62; B05D 2256/00; B05D 1/60; B05D 7/142; B05D 2202/45; C09D 4/00; C09D 179/04; C08F 238/00; C08F 8/30; C08F 293/005; C08F 2438/01; C08F 2438/03; C08G 73/0605; C08G 73/0644; C09J 179/04; G01N 33/54393

USPC ....... 428/457, 367, 364, 375, 378, 394, 408; 106/285, 287.24; 606/228, 213, 215, 231, 606/232; 57/3, 243; 525/54.1, 437, 418; 427/412.3, 255.28, 2.31, 489, 491, 331, 427/244; 623/1.11, 1.15

See application file for complete search history.

(56) References Cited

U.S. PATENT DOCUMENTS

| | | | |
|---|---|---|---|
| 4,014,973 A | 3/1977 | Thompson | |
| 4,043,344 A | 8/1977 | Landi et al. | |
| 4,047,533 A | 9/1977 | Perciaccante et al. | |
| 4,792,336 A | 12/1988 | Hlavacek et al. | |
| 5,019,093 A | 5/1991 | Kaplan et al. | |
| 5,059,213 A | 10/1991 | Chesterfield et al. | |
| 5,292,328 A | 3/1994 | Hain et al. | |
| 5,318,575 A | 6/1994 | Chesterfield et al. | |
| 5,352,392 A | 10/1994 | Johnson et al. | |
| 7,294,357 B2 * | 11/2007 | Roby | 427/2.31 |
| 2004/0258917 A1 | 12/2004 | Matsui et al. | |
| 2005/0119395 A1 | 6/2005 | Moireau | |
| 2006/0018948 A1 * | 1/2006 | Guire et al. | 424/426 |
| 2007/0244265 A1 * | 10/2007 | Matyjaszewski | C08F 8/30 525/376 |
| 2007/0272122 A1 * | 11/2007 | Lahann et al. | 106/285 |
| 2007/0293927 A1 * | 12/2007 | Frank | A61F 2/90 623/1.11 |
| 2009/0061430 A1 * | 3/2009 | Roitman et al. | 435/6 |
| 2009/0264925 A1 * | 10/2009 | Hotter | A61L 17/04 606/228 |
| 2012/0021217 A1 * | 1/2012 | Hadba et al. | 428/375 |
| 2012/0029150 A1 * | 2/2012 | Hadba et al. | 525/54.1 |

FOREIGN PATENT DOCUMENTS

| | | |
|---|---|---|
| WO | 2010095055 | 8/2010 |
| WO | 2010095057 A1 | 8/2010 |

OTHER PUBLICATIONS

International Search Report corresponding to International Application No. PCT/US2011/029864, completed on May 3, 2011 and dated May 11, 2011; 3 pages.

Le Dévédec, et al., "Separation of Chitosan Oligomers by Immobilized Metal Affinity Chromatography," J. Chromatogr A., Jun. 20, 2008; 1194(2): 165-71.

Fu, et al. "Smart Nanofibers from Combined Living Radical Polymerization, "Click Chemistry", and Electrospinning" ACS Applied Materials & Interfaces, 2009, vol. 1, No. 2, pp. 239-243.

Chang, Z. et al., "Grafting Poly(methyl methacrylate) onto Polymide Nanofibers via "Click" Reaction" ACS Applied Materials & Interfaces, 2009, vol. 1, No. 12, pp. 2804-2811.

Australian Examination Report, Application No. 2011232363 dated May 4, 2015.

European Search Report, Application No. 11 76 0259 dated Jan. 27, 2015.

* cited by examiner

ENHANCED SUTURE BRAID STRENGTH THROUGH CLICK CHEMISTRY

CROSS-REFERENCE TO RELATED APPLICATIONS

This application is a U.S. National Stage Application filed under 35 U.S.C. § 371(a) of International Application No. PCT/US2011/029864 filed Mar. 24, 2011, which claims the benefit of and priority to U.S. Provisional Patent Application Ser. No. 61/317,439 filed Mar. 25, 2010, the entire contents of which are incorporated by reference herein.

BACKGROUND

Technical Field

The present disclosure relates to yarns that contain crosslinked filaments, and more particularly to the use of click chemistry to form braided multifilament yarns, methods of preparing such yarns, and surgical devices made from such yarns.

Background of Related Art

Braided multifilaments often offer a combination of enhanced pliability, knot security, and tensile strength when compared to their monofilament counterparts. The enhanced pliability of a braided multifilament is a direct consequence of the lower resistance to bending of a bundle of very fine filaments relative to one large diameter monofilament. However, a tradeoff between braid strength and pliability exists in the design of conventional braided multifilaments.

Braided multifilaments intended for the repair of body tissues should meet certain requirements: they should be substantially non-toxic, capable of being readily sterilized, possess good tensile strength and pliability, and have acceptable knot-tying and knot-holding characteristics. If the braided multifilaments are of the bio-degradable variety, the degradation of the braided multifilaments should be predictable and closely controlled. If the braided multifilaments are a composite of different filaments or yarns, the inherent mechanical property differences between the two or more filament or yarn types can lead to components of the braid failing before the braid completely fails. This is especially true when the mechanical properties of the different filaments or yarns vary greatly.

It would be advantageous to enhance the properties of these, and other, braided multifilaments by crosslinking the filaments or yarns to increase the braid strength of these structures.

SUMMARY

The surgical devices according to the present disclosure include yarns having at least one first filament and at least one second filament. The first filament possesses a polymer core and first reactive members known to have click reactivity on a surface thereof. The second filament possesses a polymer core and second reactive members known to have click reactivity on a surface thereof. The first and second reactive members are complementary such that they interact to covalently bond the filaments together.

Methods for forming a yarn are also described. In accordance with the present methods, at least one first filament possessing a polymer core and a reactive member known to have click reactivity on a surface thereof and at least one second filament possessing a polymer core and a reactive member known to have a complementary click reactivity to the reactive member of the first filament on a surface thereof are provided. The reactive members of the first and the second filaments are crosslinked to produce a yarn.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE EMBODIMENTS

Figure 1:
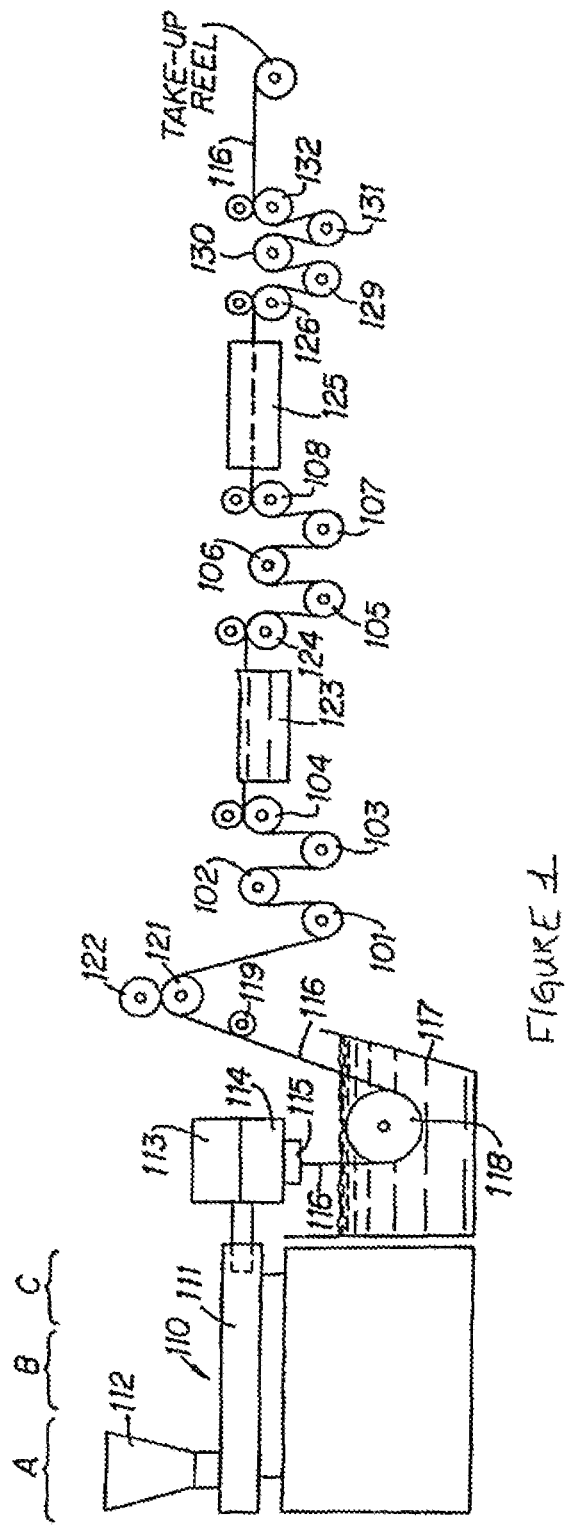
FIG. 1 is a schematic illustration of an apparatus which is suitable for carrying out a fiber manufacturing process in accordance with the present disclosure.

Filaments including functional groups having complementary click reactivity are used in accordance with the present disclosure to prepare yarns that can be incorporated into a braided, knitted, woven, or other suitable structure to provide a surgical device. The yarns include first filaments having a first functional group with click reactivity and second filaments having a second functional group having complementary click reactivity with the functional groups of the first filaments. By "complementary" it is mean that the first and second functional groups are able to specifically interact together to covalently bond the filaments together.

The yarns formed in accordance with the present disclosure may be used for a variety of surgical and wound applications. The yarns, for example, may be used alone for closing wounds and incisions in the form of multifilament sutures. The yarns may also be used in combination with the each other or other absorbable or non-absorbable yarns to form knitted, woven, or non-woven meshes or fabrics. A wide variety of surgical articles can be manufactured from the yarns of the present disclosure. These articles include, but are not limited to, sutures as discussed above, threads, rods, cables, tapes, tethers, meshes, slings, patches, wound dressings, drug delivery devices, fasteners, and other implants and composite materials such as pledgets, buttresses, adhesion barriers, and the like.

A plurality of filaments is used to form a yarn and a plurality of yarns is used to form a braid, knit or weave.

A "heterogeneous yarn" is a configuration containing at least two dissimilar filaments mechanically bundled together to form a yarn. Unlike a heterogeneous yarn, a "homogeneous" yarn is a configuration containing substantially similar filaments.

A "heterogeneous braid" is a configuration containing at least two dissimilar yarns. The two types of yarns are intertwined in a braided construction. A "homogeneous braid" then, is a configuration containing substantially similar yarns. The yarns are intertwined in a braided construction.

In the broadest sense, this disclosure contemplates yarns composed of filaments prepared from a polymer having at least one functional group known to have click reactivity at the surface thereof. The polymer used to make the filament in accordance with the present disclosure possess a core that is functionalized with one or more reactive members.

The core may be any suitable biocompatible material. The core may be a homopolymer or a copolymer, including random copolymers, block copolymers, or graft copolymers. The core may be a linear polymer, a branched polymer, or a dendrimer. The core may be a natural material or a synthetic material and may be bioabsorbable or non-bioabsorbable. It should of course be understood that any combination of natural, synthetic, bioabsorbable, and non-bioabsorbable materials may be used to form the core of the filaments.

Some non-limiting examples of synthetic materials from which the core may be prepared include, but are not limited to, polymers such as those made from alpha-hydroxy acids (e.g., lactic acid, glycolic acid, and the like), lactide, glycolide, ε-caprolactone, δ-valerolactone, carbonates (e.g., trimethylene carbonate, tetramethylene carbonate, and the like), dioxanones (e.g., 1,4-dioxanone), 1,dioxepanones (e.g., 1,4-dioxepan-2-one and 1,5-dioxepan-2-one), ethylene glycol, ethylene oxide, esteramides, hydroxy alkanoates (e.g., γ-hydroxyvalerate, β-hydroxypropionate, 3-hydroxybuterate, and the like), poly (ortho esters), tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics), copolymers and combinations thereof.

Suitable natural biodegradable polymers include, for example, collagen, cellulose, poly (amino acids), polysaccharides, chitosan and chitosan derivatives (e.g., chitosan acetate/formate polymers), hyaluronic acid, gut, copolymers and combinations thereof.

Examples of suitable non-degradable polymers from which the filaments of the surgical devices described herein may be made include, but are not limited to, fluorinated polymers (e.g., fluoroethylenes, propylenes, and fluoroPEGs), polyolefins such as polyethylene, polyesters such as polyethylene terepththalate (PET), nylons, polyamides, polyurethanes, silicones, ultra high molecular weight polyethylene (UHMWPE), polybutesters, polyaryletherketone, copolymers and combinations thereof.

In embodiments, the core may be prepared from a polyol, a polyamine, or a polythiol. Examples of such polyols include polyethers, polyesters, polyether-esters, polyalkanols, combinations thereof, and the like. In some embodiments, the polyol may be a branched polyol. Such a polyol may have a central core from which from about 3 to about 12 arms may extend, with hydroxyl groups at the free terminal of each arm. In embodiments, the polyol may be endcapped with functional groups. Methods for endcapping the polyol to provide a reactive end group are within the purview of those skilled in the art.

In some embodiments, polyrotaxanes may be utilized as a core material. Polyrotaxane materials include cyclic molecules, linear molecules threaded through the cyclic molecules, and optionally bulky end groups on the linear molecules to prevent the loss of the cyclic molecules by dethreading. Examples of suitable polyrotaxanes include those created by linear polymers such as poly(ethylene oxide) (PEO) penetrating the inner cavity of cyclodextrins (CDs) to form inclusion complexes with a necklace-like supramolecular structure.

In preparing filaments in accordance with the present disclosure, the polymer may be commercially available pre-functionalized cores or may be synthesized. It is contemplated that a plurality of different reactive members may be present and that they may be terminally located, or alternatively located along the length of the polymer chain. In embodiments, the polymer has from about 2 to about 50 reactive members. In embodiments, the polymer may be functionalized by converting an attached functional unit on the core thereby providing site specific functional materials, site specific functional materials comprising additional functionality, or chain extended functional materials. Optionally, a linker may or may not be present for linking a functional group to the core. These reactive members may form arms extending from the core. Such cores may thus be linear, branched, star-shaped, dendrimeric, and the like.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions. These reactions represent highly specific reactant pairs that have a chemoselective nature, meaning that they mainly react with each other and not other functional groups.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkly/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

a)

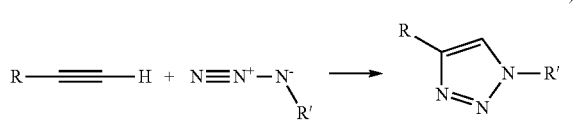

where R and R' are the core of the polymer.

The Diels-Alder reaction combines a diene (a molecule with two alternating double bonds) and a dienophile (an alkene) to make rings and bicyclic compounds. Examples include:

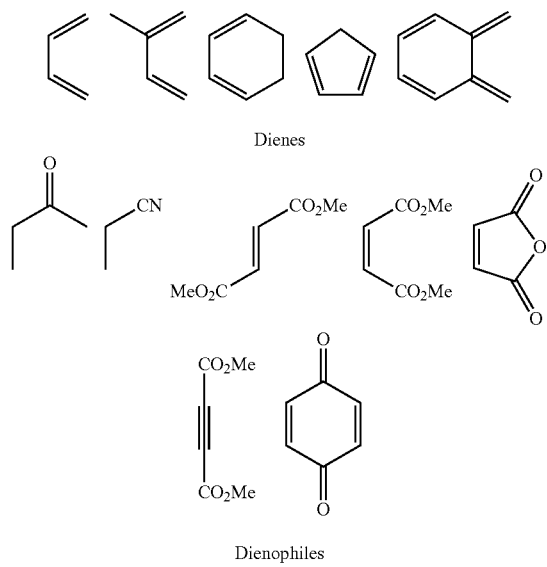

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

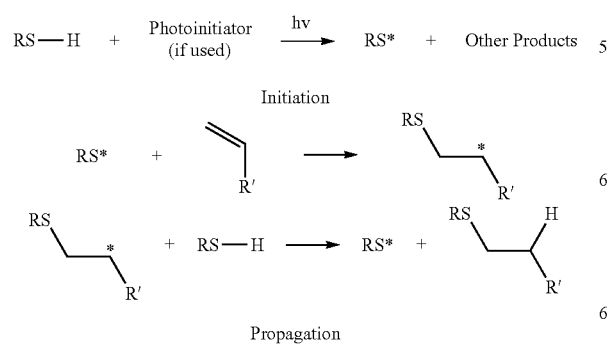

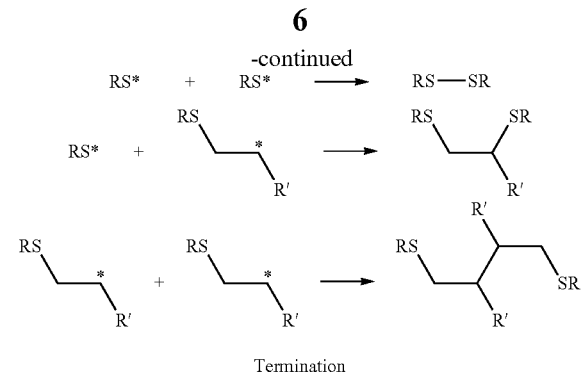

Termination

Other examples of the types of reactions that are known to have click reactivity include a hydrosilation reaction of H—Si and simple non-activated vinyl compounds, urethane formation from alcohols and isocyanates, Menshutkin reactions of tertiary amines with alkyl iodides or alkyl trifluoromethanesulfonates, Michael additions, e.g., the very efficient maleimide-thiol reaction, atom transfer radical addition reactions between —SO2Cl and an olefin ($R^1,R^2$—C=C—$R^3,R^4$), metathesis, Staudinger reaction of phosphines with alkyl azides, oxidative coupling of thiols, many of the procedures already used in dendrimer synthesis, especially in a convergent approach, which require high selectivity and rates, nucleophilic substitution, especially of small strained rings like epoxy and aziridine compounds, carbonyl chemistry like formation of ureas, and addition reactions to carbon-carbon double bonds like dihydroxylation. Therefore, attached functionality may be chosen from acetylene bond, an azido-group, a nitrile group, acetylenic, amino group, and phosphino group. The click chemistry reaction may results in the addition of a functional group selected from amino, primary amino, hydroxyl, sulfonate, benzotriazole, bromide, chloride, chloroformate, trimethylsilane, phosphonium bromide or bio-responsive functional group including polypeptides, proteins and nucleic acids, to the polymer.

Thus, suitable reactive members that may be applied to the core include, for example, an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as —$CO_2N(COCH_2)_2$, —$CO_2N(COCH_2)_2$, —$CO_2H$, —CHO, —$CHOCH_2$, —N=C=O, —$SO_2CH=CH_2$, —$N(COCH)_2$, —S—S—($C_5H_4N$), and/or groups of the following structures wherein X is halogen and R is hydrogen or $C_1$ to $C_4$ alkyl:

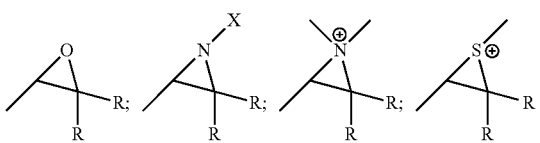

The core of the polymer can be provided with click reactive members using any variety of suitable chemical processes.

For example, the monomers from which the core is made can be functionalized so that the reactive members appear along the length of the core. In such embodiments, monomers can be initially functionalized with a group such as a halogen to provide a reactive site at which the desired first click reactive member can be attached after polymerization.

Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with the first reactive member. For example, the halogenated polyester can be reacted with sodium azide to provide azide groups along the polymer chain or with propagyl alcohol to provide alkyne groups along the polymer chain. See, R. Riva et al., *Polymer* 49, pages 2023-2028 (2008) for a description of such reaction schemes. In another example, a propargyl group may be introduce into a cyclic carbonate monomer to form 5-methyl-5-propargyloxycarbonyl-1,3-dioxan-2-one (MPC) which is polymerizable with lactide to form p(LA-co-MPC). See, Q. Shi et al., *Biomaterials*, 29, pages 1118-1126 (2008). Alternatively, the polymer or copolymer backbone may be halogenated using methods similar to those described by Nottelet et al., *Biomaterials*, 27, pages 4948-4954 (2006). Once halogenated, the backbone can be functionalized with a click reactive functionality by reacting it with a hydroxy-acid under condition described by Shi et al. *Biomaterials*, 29, pages 1118-1126 (2008) followed by reaction with sodium azide. The halogen may also be converted directly to the alkyne by reacting it with an alcoholic alkyne such as propargyl alcohol. The entire disclosure of each of these articles is incorporated herein by this reference.

Those skilled in the art reading this disclosure will readily envision chemical reactions for activating other core materials to render them suitable for use in the present disclosure.

In fabricating the filament, the polymer may take the form of any solution, suspension, semi-solid, or solid material capable of allowing the polymer to be fabricated into a desired shape. The polymer may be in granular, pellet, or powder form, or alternatively, may be in a dilute solution. Suitable solvents which may be utilized to form a dilute solution include any biocompatible solvent within the purview of those skilled in the art which will not interfere with the reaction of the complementary reactive members. Suitable solvents which may be utilized include, for example, polar solvents such as water, ethanol, triethylene glycol, dimethyl sulfoxide, glymes (such as diglyme, triglyme, tetraglyme, and the like), polyethylene glycols, methoxy-polyethylene glycols, dimethylformamide, dimethylacet-amide, gamma-butyrolactone, n-methylpyrollidone, ketones such as methyl ethyl ketone, cyclohexanone, diethylene glycol momethyl ether acetate, diethylene glycol monobutyl ether acetate, diethylene glycol monomethyl ether, diethylene glycol monoethyl ether, diethylene glycol monobutyl ether, diethylene glycol monoisobutyl either, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution. The amount of solvent used will depend on a number of factors, including the particular polymer and reactive members that are to be employed and the intended end use of the composition.

In embodiments, the functionalized polymer is melt extruded to form a surface reactive filament. Known spinning apparatuses can be used for the production of filaments, in accordance with the present disclosure.

FIG. 1 schematically illustrates a filament manufacturing operation in accordance with the disclosure. Extruder unit 110 is of a known or conventional types and is equipped with controls for regulating the temperature of barrel 111 in various zones thereof, e.g., progressively higher temperatures in three consecutive zones, A, B, and C along the length of the barrel. Adding heat during the mixing and/or extruding steps aids in the curing time of the polymer, as faster curing rates are observed at higher temperatures.

Motor-driven metering pump 113 delivers the melt extruded polymer mixture at a constant rate and with high pressure to spin pack 114 and thereafter through spinneret 115 possessing one or more orifices of desired diameter to provide a molten monofilament 116 which then enters quench bath 117, e.g., containing water, where the monofilament solidifies. The distance monofilament 116 travels after emerging from spinneret 115 to the point where it enters quench bath 117, i.e., the air gap, can vary. If desired, a chimney (not shown), or shield, can be provided to isolate monofilament 116 from contact with air currents which might otherwise affect the cooling of the monofilament in an unpredictable manner. In general, barrel zone A of the extruder can be maintained at a temperature of from about 100° C. to 220° C., zone B at from about 160° C. to 230° C., and zone C at from about 170° C. to about 240° C. Additional temperature parameters include: metering pump block 113 at from about 170° C. to about 230° C., spin pack 114 at from about 170° C. to about 230° C., spinneret 115 at from about 170° C. to about 230° C., and quench bath at from about 10° C. to about 80° C.

Monofilament 116 is passed through quench bath 117 around driven roller 118 and over idle roller 119. Optionally, a wiper (not shown) may remove excess water from the monofilament as it is removed from quench bath 117. On exiting the quench bath the monofilament is wrapped around a first godet 121 provided with nip roll 122 to prevent slippage which might otherwise result from the subsequent stretching operation; and subsequently wrapped around godets 101, 102, 103 and 104 or any other suitable godet arrangement. Monofilament 116 passing from godet 104 is stretched, e.g., with stretch ratios on the order of from about 3:1 to about 10:1 and preferably from about 4:1 to about 7:1, to effect its orientation and thereby increase its tensile strength.

In the stretching operation, monofilament 116 may be drawn through hot water (or other suitable liquid medium) draw bath 123 by means of godets 124, 105, 106, 107 and 108 or any other suitable arrangement of godets which rotate at a higher speed than godet 104 to provide the desired stretch ratio. The temperature of hot water draw bath 123 is advantageously from about 30° C. to about 90° C. and preferably is from about 30° C. to about 50° C. In an alternative stretching operation, generally preferred for smaller filament sizes, e.g., sizes 3/0 to 8/0, monofilament 116 may be drawn by godets 124, 105, 106, 107, and 108 or any other suitable godet arrangement through hot air convection oven chamber 123 at a temperature of from about 30° C. to about 140° C., and preferably from about 50° C. to about 130° C. to provide the desired amount of stretch.

Following the stretching operation, monofilament 116 optionally may be subjected to an on-line annealing and/or additional stretching without shrinkage or relaxation with shrinkage operation as a result of which the monofilament shrinks. In the process of FIG. 1, on-line annealing with or without relaxation when desired is accomplished by driving monofilament 116 by godets 126, 129, 130, 131, and 132 or any other suitable godet arrangement through second hot air oven chamber 125 at a temperature of from about 40° C. to about 150° C., and preferably from about 60° C. to about 130° C. During the relaxation process, at these temperatures, monofilament 116 will generally recover to within about 80 percent to about 97 percent, and preferably to within about 95 percent, of its pre-annealed length to provide the finished filament. For relaxation, the third godet rotates at a slower speed than the second godet thus relieving tension on the filament.

Annealing of the filament also may be accomplished without shrinkage of the filament. In carrying out the annealing operation, the desired length of filament may be wound around a creel and the creel placed in a heating cabinet maintained at the desired temperature, e.g., about 60° C. to about 130° C. After a suitable period of residency in the heating cabinet, e.g., about 18 hours or so, the filament will have undergone essentially no shrinkage. Variables such as the annealing temperatures, time, and pressure may affect the curing time of the fibers as well. The creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed filament is removed from the heating cabinet and when returned to room temperature, the filament is removed from the creel, conveniently by cutting the wound monofilament at opposite ends of the creel.

In embodiments, surface reactive filaments formed from functionalized polymers having chitin or chitin derivative cores that have been functionalized with click reactive members can be produced according to the present disclosure by spinning from anisotropic solution. Suitable methods for solution spinning chitin or chitin derivative fibers in general are disclosed in European Patent Nos. EP0328050A2 and EP0077098A2, the entire disclosures of which are incorporated herein by this reference. Such fibers can have tensile properties which typically fall between 4-8 g/d tenacity and 150-250 g/d initial modulus.

High strength chitosan filaments can be prepared by spinning an aniostropic solution of chitosan or a derivative of chitin or chitosan through an inert gas and into a coagulating bath, removing the as-spun filament and treating it with alkali to remove N-acetyl, O-acetyl or other pendant groups at the 2, 3 and 6 carbon positions of the glucosamine repeating unit. Treatment of fibers is by immersion of the fibers into a solution of NaOH. With fine denier fibers, e.g., 4-5 dpf., a 5 minute immersion at 70° C. in a 50% wt. solution of NaOH is satisfactory. A 2-3 hr. exposure at 80° C. in a 30% wt. solution is useful with chitosan acetate formate filament. With chitosan acetate, temperatures in the range of 80° to 116° C. at NaOH concentration of 30% have been found useful with the higher temperatures requiring less time for completion of the reaction. Severe treatments are generally to be avoided since they may cause excessive interfilament fusion and a product of inferior quality. Conversion of the starting filament to a chitosan filament is confirmed if the chitosan filament is readily soluble in dilute (3-20% wt.) acetic acid.

Figure 2:
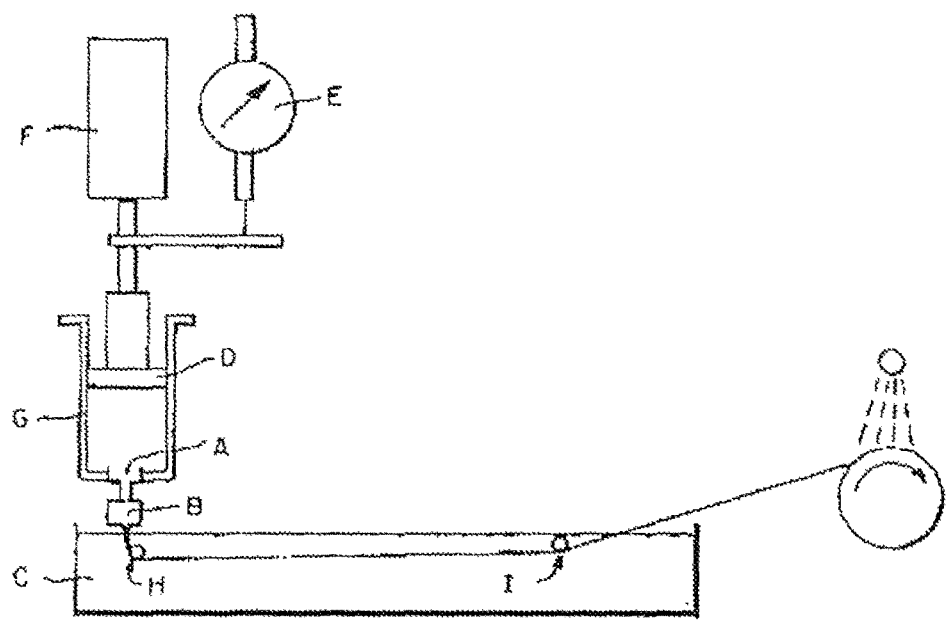
FIG. 2 is a schematic illustration of another apparatus which is suitable for carrying out a fiber manufacturing process in accordance with the present disclosure.

In using the apparatus of FIG. 2 an anisotropic solution of chitin or a chitin derivative is placed in spin cell (G). A piston (D) activated by hydraulic press (F) and associated with piston travel indicator (E) is positioned over the surface of the solution, excess air is expelled from the top of the cell and the cell is sealed. The spin cell is fitted at the bottom with the following screens (A) for solution filtration: four to six 325-mesh screens. The filtered solution is then passed into a spinneret pack (B) containing two or three 325-mesh screens. Solutions are extruded through an air gap at a controlled rate into a static bath (C) using a metering pump to supply pressure at piston (D). The filament is passed around a pin (H), pulled through the bath, passed under a second pin (I) and wound onto a bobbin. The air gap between the spinneret face and the coagulation bath is typically 0.6 to 2.0 cm. The coagulation bath temperature is generally held below 100° C.

Figure 3:
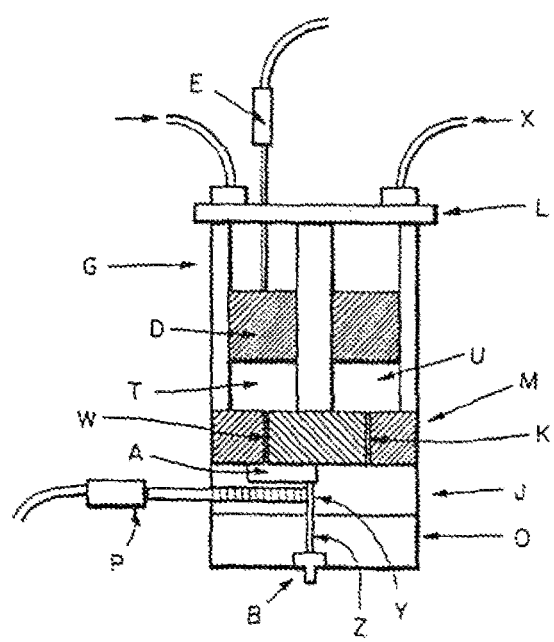
FIG. 3 is a cross-sectional view of yet another embodiment of a fiber manufacturing process in accordance with the present disclosure.

In using the apparatus of FIG. 3, filter plate (J) is replaced by mixing plate (R). Polymer dope is placed in cylinder bore (T) and then piston (D) and cap plate (L) is fitted to the spin cell (G). A driver fluid (e.g. water) is pumped into the upper part of bore (T) through feed line (F). The piston (D) is displaced by the driver fluid, thereby pushing the polymer dope through passages (W), (S) in mixing plate (R) and then through passage (K) in distribution plate (M) into second cylinder bore (U). This process is then reversed by pumping fluid through feed line (X). The aforementioned forward and reverse process is repeated several times to effect a mixing of the polymer dope. Component (E) acts to sense the position of cylinder (D).

After mixing is complete (about 30 cycles), mixing plate (R) is replaced by filter plate (J) and polymer dope is extruded from bore (T) through passage (W), through filter pack (A) containing 2 Dutch Twill Weave 165×800 mesh screens, through passage (Y) in filter plate (J) and passage (Z) in spinneret mounting plate (O) and out of spin cell (G) through spinneret (B). The extruded dope is spun into a bath and taken up as described for FIG. 2. Pressure of the polymer dope during spinning is measured by pressure transducer (P).

In other embodiments, filaments having collagen or collagen derivative cores that have been functionalized with click reactive members can be produced according to the present disclosure by gel spinning. Suitable methods for gel spinning collagen filaments in general are disclosed in U.S. Pat. Nos. 5,562,946 and 5,911,942, the entire disclosures of which are incorporated herein by this reference.

Figure 4:
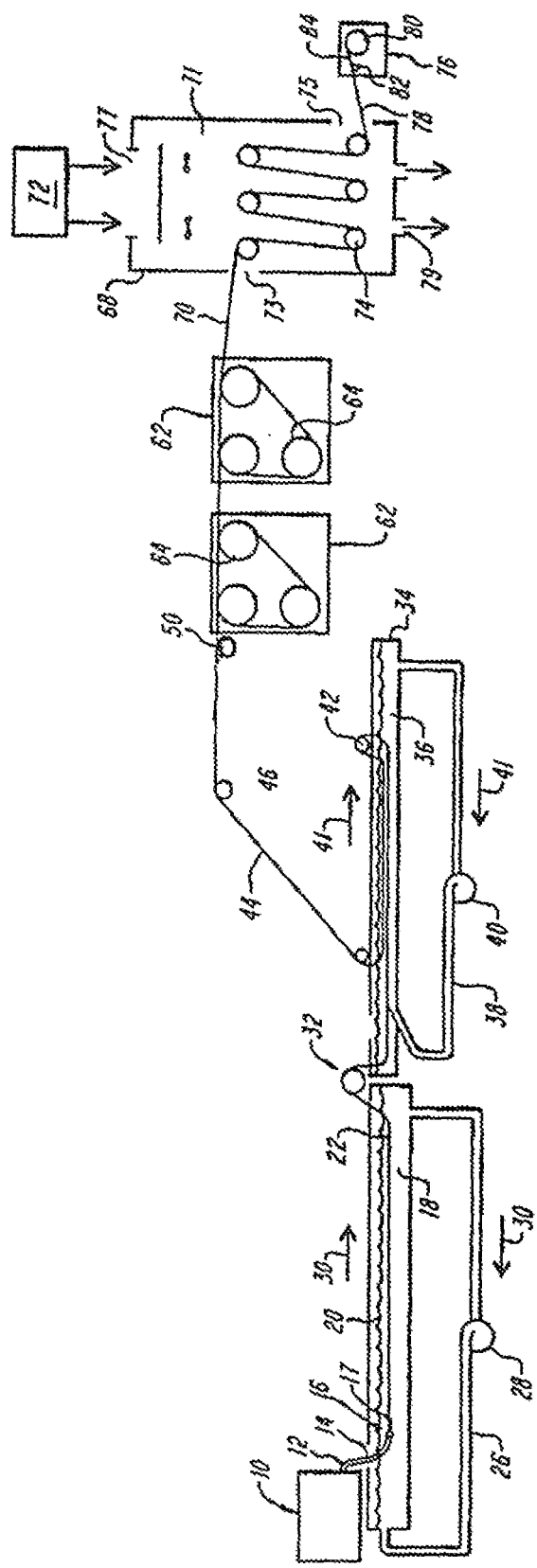
FIG. 4 is a schematic illustration of another apparatus suitable for spinning fibers in accordance with the present disclosure.

In an illustrative apparatus for gel spinning such filaments shown in FIG. 4, collagen reservoir chamber 10 holds a liquid collagen solution. In one embodiment, a suitable chamber is a stainless steel syringe. Reservoir tube 12 is attached to collagen reservoir chamber 10 for directing collagen solution from collagen reservoir chamber 10 through infusion pump 14 to spinneret 16. Infusion pump 14 is capable of raising the pressure of the collagen material such that it can be extruded through spinneret nozzle 17 of spinneret 16. In embodiments, a positive displacement metering pump is used. Spinneret 16 can be single bore or multiple bore to produce monofilament or multifilament filaments, respectively. The spinneret bores can be of various diameters or have tapered profiles to form filaments of different sizes and tensile strengths. Co-component fibers can be produced with other specialized spinnerets as are known in the art. In one embodiment, spinneret nozzle 17 has diameters in the range of between about 100 and 1,000 microns.

Coagulation bath 18 has a coagulation solution 20 that can cause the liquid collagen to form a collagen gel, such as a 0.75% alkaline alginic acid in a boric acid buffer or sugar solutions or polyethylene glycol solution which also has hydrophilic properties. The opening of spinneret is immersed in a flowing coagulation solution 20. Coagulation bath 18 is suitably sized for allowing extrusion of filaments from spinneret 16 through coagulation solution 20 while having a sufficient residency time for collagen gel filament 22 to form. Coagulation bath 18 can be heated and instrumented for monitoring the relevant process variables such as temperature, pH, and velocity. Coagulation bath 18 allows collagen gel filament 22 to be formed in a horizontal trough or in a tube or vertically in a tube. Coagulation bath 18 is configured to allow circulation of coagulation solution 20 through recirculating loop 26 by circulating pump 28. Coagulation bath flow can be in the same direction 30 of fiber travel. At the end of the coagulation bath 18, roller 32 is for directing fiber out of the coagulation bath. Roller 32 is motorized and can be activated to wind collagen gel filament 22 and subsequently tow collagen gel filament 22 at desired speeds.

Dehydrating bath 34 is adjacent to roller 32 and coagulation bath 18 and is configured to allow filament 22 to be drawn into dehydrating bath 34 from roller 32. Dehydrating bath 34 holds dehydrating solution 36, such as 90% ethanol, which allows further dehydration and annealing of the filament and promotes polymerization of the collagen to improve fiber strength. An example of another suitable dehydration solution composition is acetone. Dehydrating bath 34 is configured to allow variable circulation of dehydrating solution 36 through recirculating loop 38 by circulating pump 40 which can be adjusted directionally, such as direction 41 or in the opposite direction. Return rollers 42, which can be near each end of dehydrating bath 34, allow the fiber path to be lengthened by doubling back to make any number of multiple passes through dehydrating bath 34 to allow further dehydration and promote polymerization of the collagen.

Partially dehydrated filament 44 is wound around roller 46 to second roller 50 and then to stretching roller means 62, wherein the filament can undergo a controlled deformation by being stretched between two groups of rollers 64 rotating at slightly different rates of speed. The speed of rotation of rollers 64 can be precisely controlled with digital microprocessors arranged in a closed feedback loop. The filaments are wrapped around each roller 64 several times to prevent fiber slippage relative to the roller surfaces. Roller 64 surfaces can be made of a polymer or a hardened metal resistant to corrosion. Roller 64 rotations can be adjusted individually to allow the filament to be stretched beyond the elastic yield point to produce a longer fiber of reduced diameter. Stretching roller means 62 can operate under semi-dry or dry conditions and also under high moisture content atmosphere.

Drying cabinet 68 has opening 73 for receiving stretched filament 70 from stretching rollers 62. Drying cabinet 68 has passage 71 through drying cabinet 68 for receiving warm, dry filtered air or a dry inert gas, such as dry nitrogen gas, from gas source 72 at a suitable temperature and humidity for drying stretched filament 70. The air can be passed through air passage opening 77 into passage 71 and exits through air passage opening 79. In embodiments, the temperature of the air is between about 35° C. and about 39° C. The humidity is in the range of between about 10 and about 20 percent relative humidity. Drying cabinet 68 has a series of rollers 74 which allows stretched filament 70 to remain in drying cabinet 68 while being rolled, thereby increasing the residence time of filament 70 in drying cabinet 68. Drying cabinet rollers 74 are adjustable in distance between each other and to compensate for the fiber line speed. Drying cabinet rollers 74 can be driven at a surface roller speed that can be synchronized with that of stretching roller means 62. Drying cabinet 68 has a door to provide access to the rollers for threading the leader thread.

Take-up winder 76 is for receiving dried filament 78 from exit 75 of drying cabinet 68. Take-up winder 76 has spool 80 for receiving dried filament on a removable spindle bobbin. Take-up winder 76 has a slip clutch 82 to provide a constant filament line tension and filament line speed as the spooled filament rotates radially around spool 80. Fiber spool 80 can wind the filament level or by randomly winding with the take-up winder 76.

In each case (melt extrusion, solution spinning, or gel spinning), the resulting filament possesses click reactive functional groups at the surface thereof.

Alternatively, a composition containing the functionalized polymer may be applied to a formed polymeric filament employing techniques known to one skilled in the art, e.g., dipping, wiping, spraying, total immersion, co-extrusion, etc. For example, the coating may be applied by passing the filament through a solution of the polymer, passing the filament past a brush or other coating solution applicator, or passing the filament past one or more spray nozzles dispensing the coating solution. The filament, wetted with the coating composition, can be passed through or held in a drying oven for a time and at a temperature sufficient to vaporize and drive off the solvent.

In embodiments, the surface of the formed polymeric filament may be modified prior to application of the functionalized polymer. For example, in embodiments, the surface of the filament may be activated by acid or base hydrolysis, or by plasma treatment.

The process of hydrolysis is conducted in the presence of an aqueous solution of a base or an acid to accelerate surface reaction, inasmuch as excessively long processes of activation can induce a reduction in molecular weight and thus in the mechanical properties of the material. Suitable bases for use in the present hydrolysis processes include, for example, strong alkalis such as LiOH, $Ba(OH)_2$, $Mg(OH)_2$, NaOH, KOH, $Na_2CO_3$, $Ca(OH)_2$ and weak bases such as, for example, $NH_4OH$ and amines such as methylamine, ethylamine, diethylamine and dimethylamine. Acids suitable for surface hydrolysis treatments can be chosen, for example, from among HCl, $HClO_3$, $HClO_4$, $H_2SO_3$, $H_2SO_4$, $H_3PO_3$, $H_3PO_4$, HI, $HIO_3$, HBr, lactic acid, and glycolic acid.

Surface activation by means of hydrolysis can be conducted at temperatures preferably comprised between 0° C. and the material softening temperature or glass transition temperature. Surface hydrolysis treatment is followed by careful washing to remove all traces of the acid or base. Once the surface of the filament is acid or based treated, the composition containing the functionalized polymer may be applied as described above.

Plasma treatment of the filament may result in chemical modification of the filament thereby producing sites for the covalent attachment of the functionalized polymer. Alternatively, plasma treatment may result in the deposition of a coating of a linking material to which the functionalized polymer may be covalently attached.

The term "plasma" refers to a thermodynamically non-equilibrium gaseous complex, composed of electrons, ions, gas atoms, free radicals, and molecules in an excited state, known as the plasma state. Plasma may be generated in a process known as plasma discharge by a number of methods including combustion, flames, electric discharges, controlled nuclear reactions, and shocks. The most commonly used is electric discharge.

In a typical reaction, the filament is mounted in a chamber on a steel rack. The rack is positioned between electrodes plates, one plate being connected to a radio frequency generator and the other being grounded thereby providing means for generating an electrical field between the plates in which a field of plasma can be created and sustained. A vacuum pump is utilized to reduce the pressure in the chamber, e.g., below 0.1 torr, and a valve system is operated to permit reacting gas monomers from a gas source to flow into the chamber for approximately 10 minutes before generating a plasma. The plasma is created by supplying power to the generator at a minimal level to sustain the plasma, generally 50 to 100 watts. The reaction between the plasma and the filament surface is allowed to proceed for a period of time determined by the desired thickness and surface energy of the filament, as well as the concentration of gas monomers in the reacting vapor. Typical reaction times are about 15 seconds to about 60 minutes. The thickness of the treated surface layer of the filament may be between about 100 Angstroms to about 1500 Angstroms, in embodiments between about 200 Angstroms and about 1000 Angstroms. Thereafter, the flow of gas and the power from the generator may be turned off and the valve system may be opened to permit purge gas to flow into the chamber from a gas source to purge the filament's surface of highly reactive radicals which could cause premature contamination of the filament's surface. The valve is then closed and the chamber opened to return it to atmospheric pressure, and the plasma treated filament is removed.

In other embodiments, the filaments in accordance with the present disclosure are subjected to a plasma polymerization process to form a polymer coating on at least a portion of the surface of the filament. Plasma coating methods are disclosed, for example in U.S. Pat. No. 7,294,357, the entire disclosure of which is incorporated herein by this reference.

The monomers used to form the polymer coating are polymerized directly on the filament's surface using plasma-state polymerization techniques generally known to those skilled in the art. See e.g., Yasuda, Plasma Polymerization, Academic Press Inc., New York (1985), the entire disclosure of which is incorporated herein by reference. In brief, the monomers are polymerized onto the filament surface by activating the monomer in a plasma state. The plasma state generates highly reactive species, which form the characteristically highly cross-linked and highly-branched, ultra-thin polymer coating, which is deposited on the filament surface as it moves through the area of the reactor having the most intense energy density, known as the plasma glow zone.

For plasma polymerization to produce a coating on a filament, which may also be called "plasma grafting," a suitable organic monomer or a mixture of monomers having polymerizable unsaturated groups is introduced into the plasma glow zone of the reactor where it is fragmented and/or activated forming further excited species in addition to the complex mixture of the activated plasma gases. The excited species and fragments of the monomer recombine upon contact with the filament surface to form a largely undefined structure which contains a complex variety of different groups and chemical bonds and forms a highly cross-linked polymer coating on the filament surface. If $O_2$, $N_2$, or oxygen or nitrogen containing molecules are present, either within the plasma reactor during the polymer coating process, or on exposure of the polymer coated filament to oxygen or air subsequent to the plasma process, the polymeric deposit will include a variety of polar groups.

The amount and relative position of polymer deposition on the filaments are influenced by at least three geometric factors: (1) location of the electrodes and distribution of charge; (2) monomer flow; and (3) filament position within the reactor relative to the glow region. As filaments may be pulled continuously through the plasma chamber, the influence of the filament position is averaged over the length of the fibers.

In practice, an electric discharge from an RF generator is applied to the "hot" electrodes of a plasma reactor. The selected monomers are introduced into the reactor and energized into a plasma, saturating the plasma glow zone with an abundance of energetic free radicals and lesser amounts of ions and free electrons produced by the monomers. As the filament passes through or remains in the plasma glow zone, the surface of the filament is continually bombarded with free radicals, resulting in the formation of the polymer coating.

Once a surface of the filament is plasma treated (either to provide active sites or a coating of a material containing active sites), the composition containing the functionalized polymer may be applied as described above.

Figure 5:
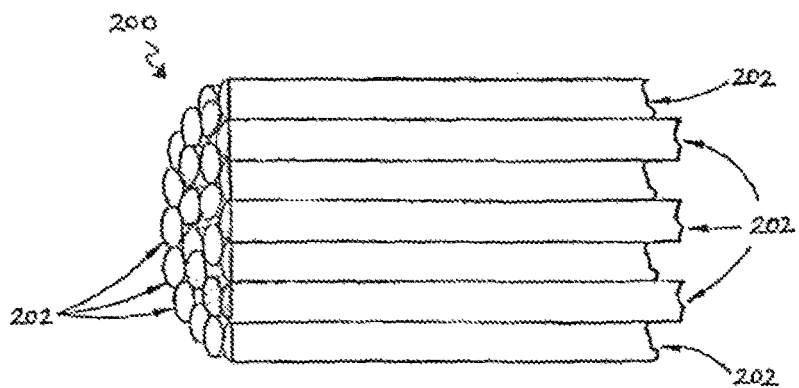
FIGS. 5 and 6 show illustrative embodiments of yarns in accordance with the present disclosure.

After the functionalized filaments are formed, they may be commingled to form yarns. The filaments may be systematically or randomly arranged within a yarn such as by twisting, plaiting, braiding, or laying the filaments substantially parallel to form the yarn. FIG. 5 illustrates a homogeneous yarn 200 including a plurality of substantially similar filaments 202 having the same polymeric core material. In embodiments, the polymer core of the filaments 202 may be functionalized with the same or different reactive members.

Figure 6:
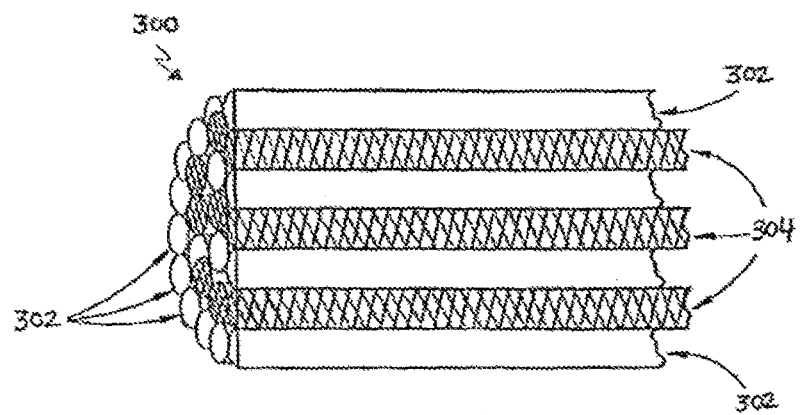

A heterogeneous yarn 300, on the other hand, contains a plurality of two or more dissimilar filaments 302, 304 as shown in FIG. 6. The first filaments 302 are made from a first polymeric core material and the second filaments 304 are made from a second polymeric core material. In embodiments, the first filaments 302 may be functionalized with a first reactive member and the second filaments 304 may be functionalized with a second reactive member which is complementary to the first reactive member.

Figure 9:
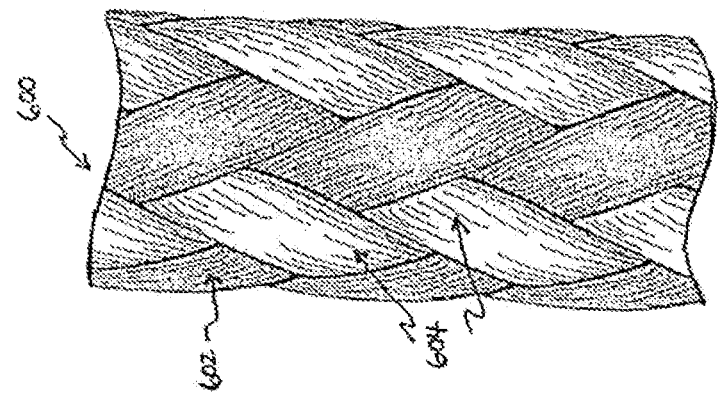
FIGS. 7-9 show illustrative embodiments of braids in accordance with the present disclosure.
Figure 8:
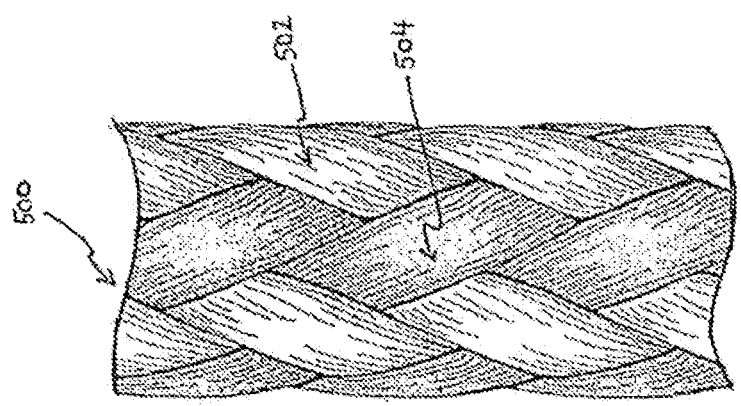
Figure 7:
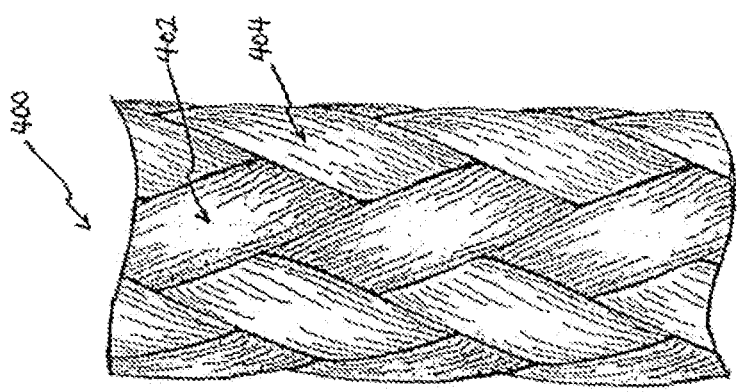

Referring now to FIGS. 7-9, braids are formed from yarns in accordance with the present disclosure. As shown in FIG. 7, a braid 400 contains two similar heterogeneous yarns 402, 404. Each heterogeneous yarn contains a plurality of two dissimilar filaments. In embodiments, first filaments include first reactive members on surfaces thereof and second filaments include second, complementary reactive members on surfaces thereof. The yarns 402, 404 are intertwined to form a substantially homogeneous braid 400.

FIG. 8 illustrates a heterogeneous braid 500 containing two dissimilar yarns 502, 504. In embodiments, a first yarn 502 contains a plurality of filaments made from the same polymeric material and a second yarn 504 contains a plurality of filaments made from a different polymeric material. The first yarns 502 and/or second yarns 504 may be functionalized with the same or different reactive members. For example, in embodiments, the first yarns 502 may all be functionalized with the same reactive members and the second yarns 504 may all be functionalized with the same reactive members which are complementary to the reactive members of the first yarns. In other embodiments, the first and second yarns 502, 504 may each include a portion of filaments functionalized with a first reactive member and a portion of filaments functionalized with a second reactive member which is complementary to the first reactive member. The homogeneous first and second yarns 502, 504 are intertwined to form a heterogeneous braid 500.

In another embodiment shown in FIG. 9, a heterogeneous braid 600 contains a heterogeneous yarn 602 and a homogeneous yarn 604 which are intertwined to form a heterogeneous braid 600.

A yarn and/or braid can be prepared using conventional braiding, weaving, or other technology and equipment commonly used in the textile industry and in the medical industry for preparing multifilament braids. Such braiding machines include, for example, those sold by Steeger USA, Inc. of Spartanburg, S.C., or by the New England Butt Division of Wardwell Braiding Machine Company. Suitable braid constructions include, for example tubular, hollow, and spiroid braids and are disclosed, for example, in U.S. Pat. Nos. 3,187,752; 3,565,077; 4,014,973; 4,043,344; 4,047, 533; 5,019,093; and 5,059,213, the disclosures of which are incorporated herein by reference. Illustrative flat braided structures (suitable, e.g., for tendon repair) which can be formed using the presently described yarns include those described in U.S. Pat. Nos. 4,792,336 and 5,318,575. Suitable mesh structures are shown and described, for example, in U.S. Pat. No. 5,292,328.

The complementary reactive members provided on the formed yarn and/or braid may crosslink upon contact with each other to form an article with enhanced properties. The rate of cross-linking of the first and second filaments of the present disclosure may be tailored by controlling the concentration of the first reactive members and the second reactive members. Generally, a faster cross-link time may be observed at a higher concentration of either the first or second reactive members than the rate observed for the same components at a lower concentration. In embodiments, the ratio of first reactive members to second reactive members is from about 1:2 to about 1:1. Crosslinking may also be affected by process controls such as temperature, time, and pressure exerted on the yarns and/or braid. In other embodiments, a catalyst may be utilized to aid the formation of covalent bonds between the filaments of the yarns and/or braids.

In embodiments, a transition metal catalyst may be utilized to aid in crosslinking of the filaments. The transition metal catalyst may be copper, zinc, iron, aluminum, magnesium, and alloys thereof. In embodiments, the use of copper catalysts, such as Cu(I) catalysts, may accelerate the process. Suitable copper catalyst which may be utilized include, but are not limited to, copper sulfate, copper iodide, copper (II) sulfate in combination with ascorbic acid, combinations thereof, and the like. In embodiments, the copper catalyst may include copper sulfate, in embodiments, $CuSO_4,5H_2O$.

The transition metal catalyst may contact the yarns and/or braids at one or more points in the yarn or braid formation process. For example, a formed yarn or braid may be stretched between opposed copper surfaces. As another example, the formed yarn or braid may be passed through a quench bath containing the transition metal catalyst to crosslink the filaments. The use of a quench bath to crosslink the first and second reactive members is particularly useful where the filaments are made from a hydrophilic polymer or in a solution or gel spinning process. In some embodiments, the transition metal catalyst may be present on one or more surfaces of the braider using a chelating matrix of the type used in immobilized metal affinity chromatography. For example, a suitable chelating matrix can be prepared by derivatization of hydroxyl groups with iminodiacetic acid (IDA), carboxymethyl aspartic acid (CM-Asp) and with tris(carboxymethyl)ethylenediamine (TED) on agarose beads, as well as silica gel functionalized with IDA. The preparation of such chelating matrices is disclosed in Le Dévédec et al., "Separation of chitosan oligomers by immobilized metal affinity chromatography," *J Chromatogr A.*, 2008 Jun. 20; 1194(2):165-71, the entire disclosure of which is incorporated herein by this reference.

In embodiments, crosslinking is accomplished by irradiation with light at a wavelength of between about 20-400 nm, in the ultraviolet range. The UV radiation may be obtained from sunlight or special lamps or light sources which emit UV light having a wavelength in the range above. Particularly, thiol-ene polymerizations are photochemically initiated, step growth, free-radical processes that take place between thiols and alkenes via a sequential propagation/chain-transfer process. Thiol-ene systems form ground state charge transfer complexes, and therefore photopolymerize even in the absence of initiators in reasonable polymerization times. Since the complex which absorbs the light is consumed by the polymerization, the polymer itself does not absorb light. Thus, UV irradiation will provide surface cross-linking.

The yarns and/or braids may be irradiated with light at one or more points in the yarn or braid formation process. For example, after exiting the braider the yarn and/or braid may be irradiated with UV light to crosslink the finished fiber. The rate of cross-linking of the reactive members of the present disclosure may be controlled by varying the UV intensity or exposure time.

The yarns may further be use for delivery of a bioactive agent. Thus, in some embodiments, at least one bioactive agent may be combined with the polymer core and/or may be separately applied to individual filaments or the finished yarn. The agents may be freely admixed with the polymer core (making sure not reactive with them) or may be tethered to the polymer core through any variety of chemical bonds. In these embodiments, the present yarns can also serve as a vehicle for delivery of the bioactive agent. The term "bioactive agent," as used herein, is used in its broadest sense and includes any substance or mixture of substances that have clinical use. Consequently, bioactive agents may or may not have pharmacological activity per se, e.g., a dye or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present filaments or yarns in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent in the bioactive coating of the present disclosure include: triclosan, also known as 2,4,4'-trichloro-T-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides, such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; antimigraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; antivirals; anticoagulants; anticonvulsants; antidepressants; antihistamines; and immunological agents.

Other examples of suitable bioactive agents which may be included in the coating composition include viruses and cells; peptides; polypeptides and proteins, as well as analogs, muteins, and active fragments thereof; immunoglobulins; antibodies; nobodies; cytokines (e.g., lymphokines, monokines, chemokines); blood clotting factors; hemopoietic factors; interleukins (IL-2, IL-3, IL-4, IL-6); interferons (β-IFN, (α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins; fibrin; thrombin; fibrinogen; synthetic thrombin; synthetic fibrin; synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists and protein agonists; nucleic acids such as antisense molecules, DNA, DNA intercalators, RNA, and RNAi; oligonucleotides; polynucleotides; and ribozymes.

Devices formed with the yarns of the present disclosure may be at least partially coated with a bioresorbable coating by a surface treatment for enhanced properties. For example, the coating may be collagen, chitosan, polysaccharides, or mixtures thereof. The polysaccharides may be hyaluronic acid, alginic acid, polyglucuronic acid, chitosan, starch, soluble cellulose derivatives, and mixtures thereof. Such a coating makes it possible to eliminate crevices which may form during the construction and interplay of the fibers where bacteria or inflammatory cells may develop, thus making it possible to reduce the risk of inflammation and sepsis by preventing the installation of undesirable bacteria and/or microorganisms and/or inflammatory cells into the filled or covered crevices.

Other aspects of the invention are defined in the following clauses:

Clause 1. A yarn comprising:
at least one first filament possessing a polymer core and a first reactive member known to have click reactivity on a surface of the at least one first filament; and
at least one second filament possessing a polymer core and a second reactive member on a surface of the at least one second filament, the second reactive member being known to have complementary click reactivity to the first reactive member of the first filament.

Clause 2. The yarn according to clause 1, wherein the polymer core of the first and second filaments are the same polymeric material.

Clause 3. The yarn according to clause 1, wherein the polymer core of the first and second filaments are different polymeric materials.

Clause 4. The yarn according to any one of clauses 1-3, wherein the first and second reactive members are selected from the group consisting of amine, sulfate, thiol, hydroxyl, azide, alkyne, alkene, and combinations thereof.

Clause 5. The yarn according to any one of clauses 1-3, wherein the first and second reactive members are selected from the group consisting of carboxyl groups, aldehyde groups, sulfone groups, vinylsulfone groups, isocyanate groups, acid anhydride groups, epoxide groups, aziridine groups, episulfide groups, and combinations thereof.

Clause 6. A surgical device comprising:
first yarns comprising a plurality of filaments possessing a polymer core and reactive members known to have click reactivity on a surface thereof; and
second yarns comprising a plurality of filaments possessing a polymer core and reactive members known to have click reactivity on a surface thereof,
wherein the first yarns are interconnected with the second yarns.

Clause 7. The surgical device according to clause 6, wherein the first and second yarns are homogeneous yarns.

Clause 8. The surgical device according to clause 6, wherein the first yarns are homogeneous yarns and the second yarns are heterogeneous yarns.

Clause 9. The surgical device according to clause 6, wherein the first yarns and second yarns are heterogeneous yarns.

Clause 10. The surgical device according to any one of clauses 6-9, wherein the reactive members of the filaments of the first yarns are complementary to the reactive members of the filaments of the second yarns.

Clause 11. The surgical device according to any one of clauses 6-10, wherein the first yarns and the second yarns each contain a first portion of filaments which include first reactive members and a second portion of filaments which include second reactive members, wherein the first reactive members are complementary to the second reactive members.

Clause 12. The surgical device according to any one of claims 6-11, wherein the reactive members of the first and second yarns are selected from the group consisting of amine, sulfate, thiol, hydroxyl, azide, alkyne, alkene, and combinations thereof.

Clause 13. The surgical device according to any one of clauses 6-11, wherein the reactive members of the first and second yarns are selected from the group consisting of carboxyl groups, aldehyde groups, sulfone groups, vinylsulfone groups, isocyanate groups, acid anhydride groups, epoxide groups, aziridine groups, episulfide groups, and combinations thereof.

Clause 14. The surgical device according to any one of clauses 6-13, wherein the first and second yarns are configured to form a device selected from the group consisting of a suture, thread, rod, cable, tape, tether, mesh, sling, patch, wound dressing, drug delivery device, fastener, pledget, buttress, and adhesion barrier.

Clause 15. A method for forming yarns comprising:
providing at least one first filament possessing a polymer core and a reactive member known to have click reactivity on a surface thereof;
providing at least one second filament possessing a polymer core and a reactive member known to have a complementary click reactivity to the reactive member of the first filament on a surface thereof; and
crosslinking the reactive members of the first and second filaments to produce a yarn.

Clause 16. The method according to clause 15, wherein providing at least one first filament includes forming the at least one first filament via one of melt extrusion, solution spinning, or gel spinning.

Clause 17. The method of clause 15 or 16, wherein providing at least one second filament includes forming the at least one second filament via one of melt extrusion, solution spinning, or gel spinning.

Clause 18. The method of clause 15 or 17, wherein providing at least one first filament includes applying a composition containing the polymer core functionalized with the reactive member to the first filament.

Clause 19. The method of any one of clauses 15, 16, or 18, wherein providing at least one second filament includes applying a composition containing the polymer core functionalized with the reactive member to the second filament.

Clause 20. The method of clause 18, further comprising activating the surface of the at least one first filament prior to applying the composition containing the polymer core functionalized with the reactive member thereto.

Clause 21. The method of clause 19, further comprising activating the surface of the at least one second filament prior to applying the composition containing the polymer core functionalized with the reactive member thereto.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A heterogeneous yarn comprising:
at least one first filament possessing a polymer core functionalized to include a first reactive member known to have click reactivity on a surface of the at least one first filament; and
at least one second filament possessing a polymer core functionalized to include a second reactive member on a surface of the at least one second filament, the second reactive member being known to have complementary click reactivity to the first reactive member of the first filament, wherein the polymer core of the first and second filaments are different polymeric materials, and the first and second reactive members form a covalent bond via a reaction selected from the group consisting of a Huisgen cycloaddition reaction, a Diels-Alder reaction, a thiol-alkene reaction, and a maleimide-thiol reaction.

2. The yarn according to claim 1, wherein the first and second reactive members are selected from the group consisting of thiol, azide, alkyne, alkene, and combinations thereof.

3. The yarn according to claim 1, wherein the first reactive member comprises an azide and the second reactive member comprises an alkyne.

4. The yarn according to claim 1, wherein the first reactive member comprises a thiol and the second reactive member comprises an alkene.

5. The yarn according to claim 1, wherein the first and second reactive members form a covalent bond via a Huisgen cycloaddition reaction.

6. The yarn according to claim 1, wherein the first and second reactive members form a covalent bond via a thiol-alkene reaction.

7. The yarn according to claim 1, wherein the first and second reactive members form a covalent bond via a maleimide-thiol reaction.

8. The yarn according to claim 1, wherein the at least one first filament possessing a polymer core comprises ultra-high molecular weight polyethylene.

9. A surgical device comprising:
first yarns comprising a plurality of filaments possessing a polymer core and reactive members known to have click reactivity on a surface thereof; and
second yarns comprising a plurality of filaments possessing a polymer core and reactive members known to have click reactivity on a surface thereof,
wherein the first yarns are interconnected with the second yarns wherein the first and second yarns are the heterogeneous yarn of claim 1.

10. The surgical device according to claim 9, wherein the reactive members of the filaments of the first yarns are complementary to the reactive members of the filaments of the second yarns.

11. The surgical device according to claim 9, wherein the first yarns and the second yarns each contain a first portion of filaments which include first reactive members and a second portion of filaments which include second reactive members, wherein the first reactive members are complementary to the second reactive members.

12. The surgical device according to claim 9, wherein the reactive members of the first and second yarns are selected from the group consisting of amine, sulfate, thiol, hydroxyl, azide, alkyne, alkene, and combinations thereof.

13. The surgical device according to claim 9, wherein the reactive members of the first and second yarns are selected from the group consisting of carboxyl groups, aldehyde groups, sulfone groups, vinylsulfone groups, isocyanate groups, acid anhydride groups, epoxide groups, aziridine groups, episulfide groups, and combinations thereof.

14. The surgical device according to claim 9, wherein the first and second yarns are configured to form a device selected from the group consisting of a suture, thread, rod, cable, tape, tether, mesh, sling, patch, wound dressing, drug delivery device, fastener, pledget, buttress, and adhesion barrier.

15. A method for forming the yarn of claim 1 comprising:
providing at least one first filament possessing a polymer core and a reactive member known to have click reactivity on a surface thereof;
providing at least one second filament possessing a polymer core and a reactive member known to have a complementary click reactivity to the reactive member of the first filament on a surface thereof; and
crosslinking the reactive members of the first and second filaments to produce a yarn.

16. The method according to claim 15, wherein providing at least one first filament includes forming the at least one first filament via one of melt extrusion, solution spinning, or gel spinning.

17. The method of claim 15, wherein providing at least one second filament includes forming the at least one second filament via one of melt extrusion, solution spinning, or gel spinning.

18. The method of claim 15, wherein providing at least one first filament includes applying a composition containing the polymer core functionalized with the reactive member to the first filament.

19. The method of claim 18, further comprising activating the surface of the at least one first filament prior to applying the composition containing the polymer core functionalized with the reactive member thereto.

20. The method of claim 15, wherein providing at least one second filament includes applying a composition containing the polymer core functionalized with the reactive member to the second filament.

21. The method of claim 20, further comprising activating the surface of the at least one second filament prior to applying the composition containing the polymer core functionalized with the reactive member thereto.

* * * * *